(12) United States Patent
Dai

(10) Patent No.: US 11,421,196 B2
(45) Date of Patent: *Aug. 23, 2022

(54) HIGH DENSITY DISTRIBUTED THREE-DIMENSIONAL ELECTRODE DEVICE

(71) Applicant: Etta Biotech Co., Ltd., Jiangsu (CN)

(72) Inventor: Edward Dai, Jiangsu (CN)

(73) Assignee: ETTA BIOTECH CO., LTD., Jiangsu (CN)

( * ) Notice: Subject to any disclaimer, the term of this patent is extended or adjusted under 35 U.S.C. 154(b) by 173 days.

This patent is subject to a terminal disclaimer.

(21) Appl. No.: 16/192,077

(22) Filed: Nov. 15, 2018

(65) Prior Publication Data

US 2019/0136175 A1    May 9, 2019

Related U.S. Application Data

(63) Continuation of application No. 14/896,902, filed as application No. PCT/CN2014/079391 on Jun. 6, 2014, now abandoned.

(30) Foreign Application Priority Data

Jun. 8, 2013    (CN) .......................... 201310227093.7

(51) Int. Cl.
  *C12N 15/87*    (2006.01)
  *C12M 1/42*    (2006.01)

(52) U.S. Cl.
  CPC ............. *C12M 35/02* (2013.01); *C12N 15/87* (2013.01)

(58) Field of Classification Search
  CPC ............................... C12M 35/02; C12N 15/87
  See application file for complete search history.

(56) References Cited

U.S. PATENT DOCUMENTS 5,128,257 A * 7/1992 Baer .................... C07K 14/495
                                                    435/173.6
6,352,853 B1    3/2002 King et al.
(Continued)

FOREIGN PATENT DOCUMENTS

CN    101563132 A    10/2007
CN    101693875 A    4/2010
(Continued)

OTHER PUBLICATIONS

International Searching Authority, International Search Report and Written Opinion for PCT/CN2014/079391, dated Sep. 5, 2014.

*Primary Examiner* — Louise W Humphrey
*Assistant Examiner* — Anjali Ajit Hirani
(74) *Attorney, Agent, or Firm* — Schmeiser, Olsen & Watts, LLP

(57) ABSTRACT

Disclosed herein is a high-density distributed three-dimensional electrode device and an associated electroporation method. The method includes applying an electric pulse of a first polarity to a first group of electrodes while simultaneously applying an electrical pulse of a second polarity to a remaining group of electrodes, and then applying an electric pulse of the first polarity on a second group of electrodes while simultaneously applying an electric pulse of the second polarity to the remaining groups of electrodes. The electrodes receiving the electric pulse of the first polarity being surrounded by the electrodes receiving the electric pulse of the second polarity, and the first polarity and the second polarity are opposite.

12 Claims, 4 Drawing Sheets

(56) References Cited

U.S. PATENT DOCUMENTS

| | | | |
|---|---|---|---|
| 6,482,619 B1 | 11/2002 | Rubinsky et al. | |
| 10,731,120 B2 * | 8/2020 | Dai | C12M 35/02 |
| 10,982,182 B2 * | 4/2021 | Dai | C12M 35/02 |
| 2004/0167458 A1 | 8/2004 | Draghia-Akli et al. | |
| 2005/0043726 A1 * | 2/2005 | McHale | A61K 41/0028 606/27 |
| 2008/0063866 A1 | 3/2008 | Allen et al. | |

FOREIGN PATENT DOCUMENTS

| | | | | |
|---|---|---|---|---|
| CN | 102680526 A | 9/2012 | | |
| CN | 103275874 A | 9/2013 | | |
| WO | WO-0004949 A1 * | 2/2000 | | A61N 1/0424 |
| WO | 2005044983 A2 | 5/2005 | | |
| WO | 2005044983 A3 | 5/2005 | | |

\* cited by examiner

HIGH DENSITY DISTRIBUTED THREE-DIMENSIONAL ELECTRODE DEVICE

CROSS REFERENCE TO RELATED APPLICATIONS

This application is a continuation application of U.S. application Ser. No. 14/896,902, filed Dec. 8, 2015, which is, itself, a § 371 National Stage Application of PCT/CN2014/079391 filed Jun. 6, 2014 which claims priority to CN 201310227093.7 filed Jun. 8, 2013, which are incorporate by reference in their entirety.

TECHNICAL FIELD

The present invention relates to a cell electroporation technique, in particular a three-dimensional electrode device for electroporation.

BACKGROUND

Since 1970s, the electroporation technique was used to insert molecules into animal cells or plant cells. It is proved by researchers that exposing a cell to a short-lasted high-voltage electric field may enable formation of pathways through the cell membrane, and macromolecules such as proteins and DNAs may enter into the cell through those pathways. Those pathways are referred as electric pores which are permeability increased zone caused by a local fracture of cell membrane resulted from high voltage electric field. Although the existing times of the pores are brief, it is enough to satisfy the requirement of the macromolecules such as plasmid DNA molecules entering into the cell. The cell may tolerate the formation of the pores, however, the cell may be killed by the processes of the formation and the molecules introduced thereby if the formed pores are too much and overlarge.

At the earliest, the electroporation is carried out by using the simplest capacitor with parallel-plate, and a substantially homogeneous electric field may be formed between the electrodes opposite to each other. The cell suspension prepared for electroporation and the molecules which the operator wants to introduce are mixed and placed between the two electrodes, and a short-time high voltage electric field pulse is applied to the electrodes by one or more times such that the result of introducing the molecules into cells by electroporation can be achieved. However, the distance between the parallel-plate electrodes is large, the required voltage is usually up to several thousands volts, thus generating of cathode effect is inevasible, which has a huge damage to the cells.

Although the planar electrodes arose later solve the negative effect brought by the overhigh voltage, they are not suitable for high throughput experiment operations due to that the planer electrodes can process a very small amount of cells every time. Three-dimensional electrodes easily penetrate into tissues and living bodies, and usually use for electroporations in clinic for tumour tissues or living tissues, the electroporation efficiency of which is not high, and there is no related report of extracorporeal cell electroporation such as electroporation aimed at suspended cells or attached cells via three-dimensional electrodes.

SUMMARY

The present invention provides a high-density distributed three-dimensional electrode device, which has a simple structure and is easy to manufacture.

To solve the above-mentioned technical problems, the present invention provides a high-density distributed three-dimensional electrode device, comprising an electrode array and an electrode fixing assembly on which the electrode array is fixed, the electrode array comprising a plurality of electrodes divided into at least two groups, an electric pulse of a first polarity and an electric pulse of a second polarity are respectively applied on the at least two groups according to a time period, wherein the first polarity and the second polarity are different, and the electrodes corresponding to the electric pulse of the second polarity are distributed around the electrodes corresponding to the electric pulse of the first polarity.

In a preferred embodiment of the present invention, the plurality of electrodes in the electrode array is arranged according to an equilateral polygon, and the distances between every two adjacent electrodes in the electrode array are equal.

In a preferred embodiment of the present invention, a shape of the electrode array is an equilateral hexagon formed by several equilateral triangles, and the electrodes are located at the vertexes of the equilateral triangles.

In a preferred embodiment of the present invention, the first polarity is positive polarity and the second polarity is negative polarity.

In a preferred embodiment of the present invention, the first polarity is negative polarity, and the second polarity is positive polarity.

In a preferred embodiment of the present invention, the diameters of the electrodes are 0.01-1.2 mm, the distance between the center points of the two adjacent electrodes is 0.1-2.4 mm, the number of the electrodes is more than 5, and the number is preferred to be more than 19. The material of the electrodes is preferably stainless steel.

In a more preferred embodiment of the present invention, the diameters of the electrodes are 0.1-0.4 mm, the distance between the center points of the two adjacent electrodes is 0.2-1.5 mm, and the number of the electrodes is more than 36. The diameters of the electrodes are preferably 0.3 mm, the distance between the center points of the two adjacent electrodes is preferably 1 mm, and the number of the electrodes is preferably 37.

In a preferred embodiment of the present invention, the electrode fixing assembly comprises an electrode connecting circuit board and an electrode positioning board, the electrode connecting circuit board connecting the electrodes applied with the electric pulse of the same polarity together via a line thereon, and the electrodes being inserted into the electrode positioning board.

In a preferred embodiment of the present invention, the electrodes in the electrode array are divided into several groups, and the electrodes in the same group are only applied with the electric pulse of the same polarity, wherein one of the groups is applied with the electric pulse as a positive electrode, the rest groups are applied with the electric pulse as a negative electrode, and then another one of the groups is applied with the electric pulse as the positive electrode, the rest groups are applied with the electric pulse as the negative electrode, and alternately in this way, the obtained electric field may achieve a homogeneous electric field by superposition.

The beneficial effects of the present invention are that: the high density distributed three-dimensional electrode device of the present invention employs grouped reused electrodes; can compensate for the unevenness of the electric field caused by the three-dimensional electrode at the greatest extent; can process milliliter level of cells once; can be used in both pore plate devices and flow devices; requires a small electroporation voltage due to a small distance between the electrodes, avoiding the damage to the cells from the high voltage; low cost; is a cell electroporation device with high throughput and high efficiency.

BRIEF DESCRIPTION OF DRAWINGS

FIG. 4 is a topological structure diagram of an electrode array in the high-density distributed three-dimensional electrode device shown in FIG. 1.

Wherein reference numbers and corresponding parts are as follow: 1. electrode array, 2. electrode positioning plate, 3. electrode connecting circuit board.

DETAIL DESCRIPTION OF EMBODIMENTS

In the following, the preferable embodiments of the present invention are explained in detail combining with the accompanying drawings so that the advantages and features of the present invention can be easily understood by the skilled persons in the art, and thus it is clear to define the protective scope of the present invention.

Embodiment 1

Figure 1:
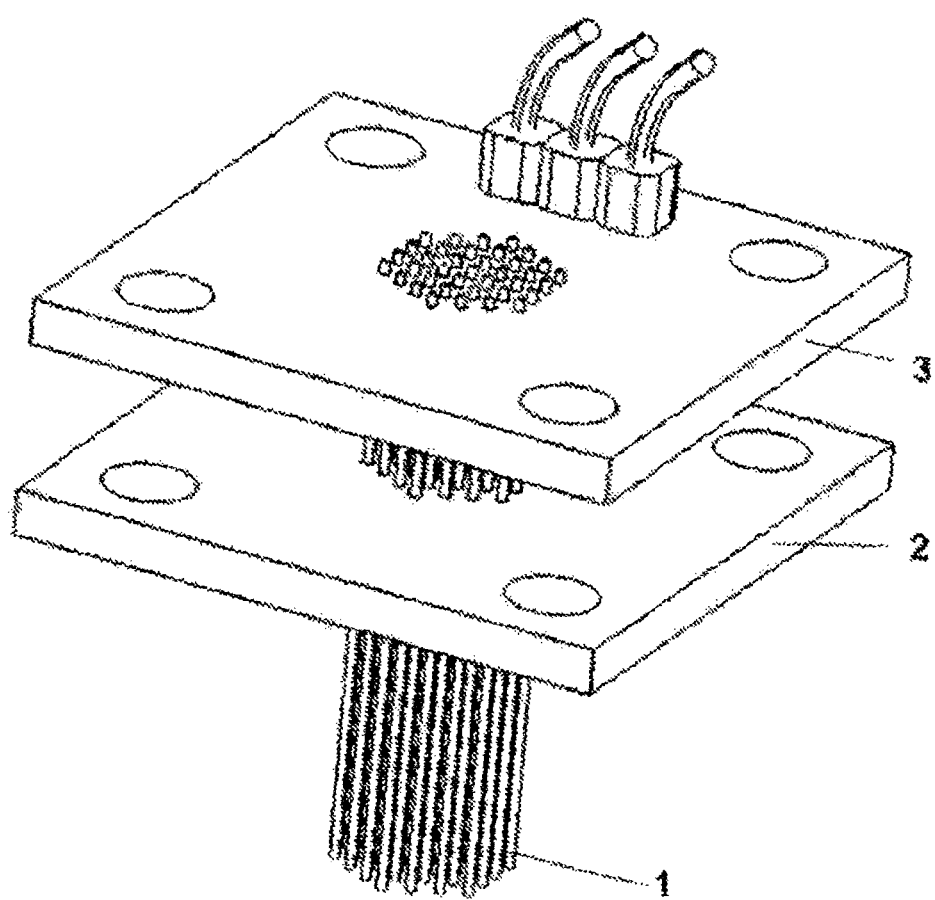
FIG. 1 is a structure schematic diagram of a preferable embodiment of a high-density distributed three-dimensional electrode device according to the present invention.
Figure 2:
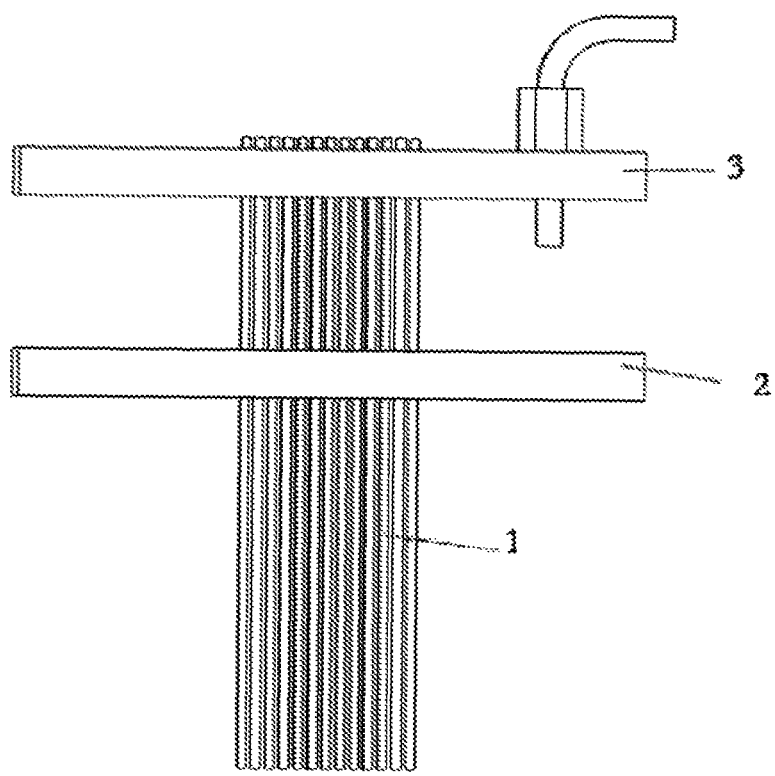
FIG. 2 is a front view of the high-density distributed three-dimensional electrode device shown in FIG. 1.
Figure 3:
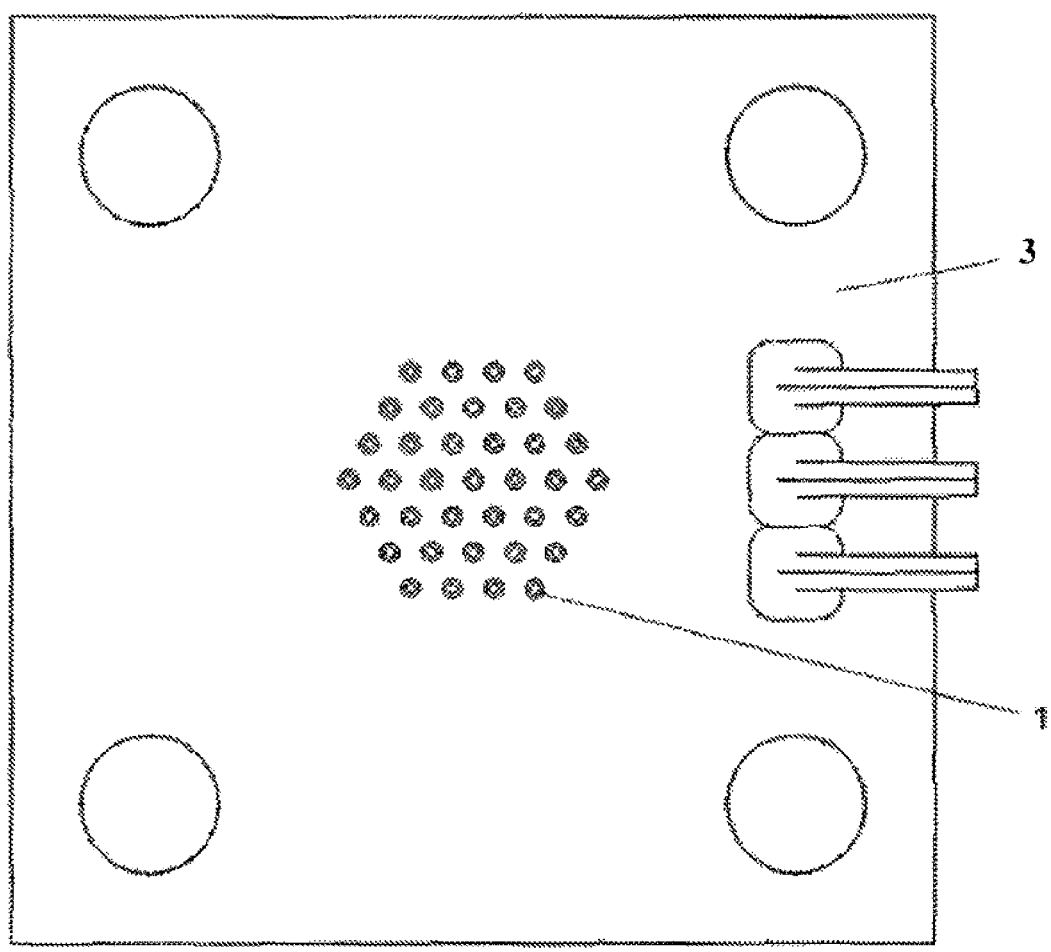
FIG. 3 is a top view of the high-density distributed three-dimensional electrode device shown in FIG. 1.
Figure 1:
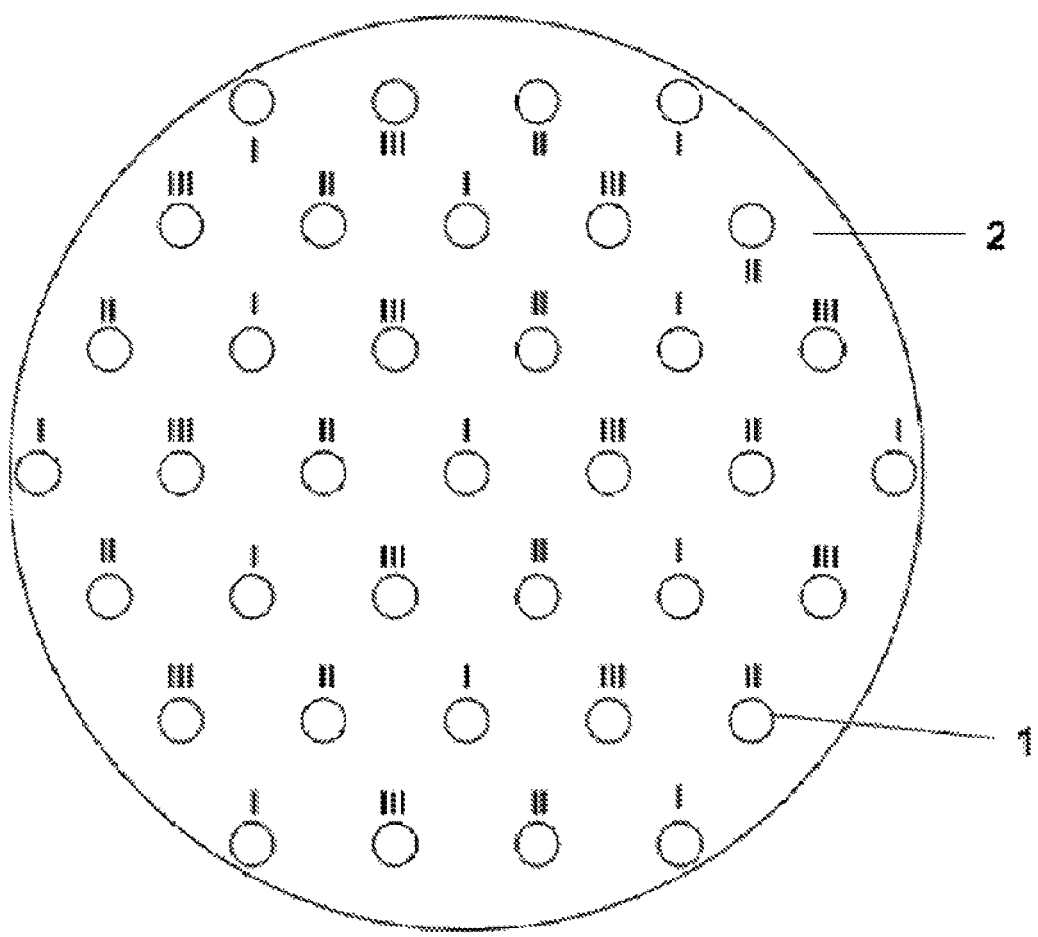

Referring to FIG. 1, FIG. 2, FIG. 3 and FIG. 4, the present invention provides a high-density distributed electrode device, comprising an electrode array 1 and an electrode fixing assembly on which the electrode array 1 is fixed.

The electrode array 1 is formed by 37 solid cylinder electrodes, and the arrangement rules are as follow: all the electrodes are arranged to be an equilateral hexagon shaped structure, the distances between two adjacent electrodes are equal, the inside of the equilateral hexagon shape is divided into several small equilateral triangle units by taking the distances between two adjacent electrodes as side length, and one electrode is placed at each vertex of the equilateral triangle units, that is, all the electrodes are divided into three groups, Group I, II and III, and vertexes of each equilateral triangle unit respectively belong to Group I, II and III.

The inner diameter of the equilateral hexagon of the electrode array 1 is matched up with the plate holes of a perforated plate, and a distance between the center points of two adjacent electrodes is 1 mm. The distance between two electrodes may affect the voltage during electroporation, and can be adjusted as required. The electrodes are inserted into the perforated plate and have a distance of 0.1 mm-1 mm from the bottom of the perforated plate.

The diameter of the electrodes is 0.3 mm, and both too large and too small diameters of the electrodes may affect the effect of the electroporation. When the diameters are too large, the effective area of electric field may be reduced, resulting in a decrease on the number of cells dealed with by electroporation, and going against highthroughput of cell electroporation. When the diameters are too small, the electrodes are easily bended resulting in a large increase of the manufacturing cost.

The material of the electrodes may be optionally selected from electric conductive metals and other electric conductive materials, wherein the stainless steel is an excellent material for electrodes. The stain steel material possesses favorable bio-compatibility, is easy to clean and not easy to be oxidized, easy to form relatively long electrodes, and is able to be mass produced and be reused for multiple times without affecting the conduction properties thereof.

The electrode fixing assembly comprises an electrode positioning board 2 and an electrode connecting circuit board 3, the electrodes are positioned by going through the electrode positioning board 2 and connected to the electrode connecting circuit board 3, and the electrode connecting circuit board 3 connects the electrodes applied with the electric pulse of the same polarity together via a line thereon. Due to that the electrodes are relatively long and the electroporation has a very high accuracy requirement for the distance between the electrodes, the electrode positioning board 2 is employed to position the electrodes in electroporation experiments. The electrode positioning board 2 can confine and position the electrodes along a long distance due to a thickness thereof is about 1 cm, and therefore, the electrodes can be controlled accurately to reach the bottom of the perforated plate. A support structure of the high density distributed three-dimensional electrode device may be easily extended to form electrode networks of any combination array such as 2*2, 1*4, 12*8 etc., and such flexible and varied combinations may be compatible with the perforated plate structure at the greatest extent, being convenient for user.

The electrode connecting circuit board 3 connects the electrodes in the same group together by welding connection, conducting adhesive or other electrical connecting manner such as printed circuit board and another component which can connect regulation lines. The electrode positioning board 2 is used for positioning the electrodes which are vimineous and easily bended. Therefore, in the embodiments of FIGS. 1-2, the electrode positioning board 2 is arranged approximately at the middle of the electrodes for positioning. The use of the electrode positioning board 2 can reduce the inconformity of the distances between the electrodes and thus improve the homogeneity of the electric field.

The high-density distributed three-dimensional electrode device may be a monoporate device, and 4, 96 or more of this device can be used to form a group to cooperate with a perforated plate structure commonly used in biology.

The electroporation method of the high-density distributed three-dimensional electrode device in the present embodiment is: during the electroporation, firstly by taking Group I as a positive electrode and Group II, III as a negative electrode the electric pulse is applied, then by taking Group II as a positive electrode and Group I, III as a negative electrode the electric pulse is applied, and then by taking Group III as a positive electrode and Group I, II as a negative electrode the electric pulse is applied.

For certain kind of cells, pores may appear on the cell membranes when the electric field is higher than a certain threshold. The death rate of the cells may arise as the electric field gradually increases. To ensure a high electroporation rate and low death rate of the cells, it is desired to accurately control the electric field to be the threshold electric field of the electroporation.

As long as the homogeneous electric field intensity is controlled to be the optimal electroporation voltage of the electroporation, cells in the whole effective area may experience electroporation at the greatest extent. It can be seen that grouping and reusing compensate for the unevenness of the electric field caused by single group, increases the electroporation efficiency, and thus it can be determined that such kind of combination of electric fields has a much higher electroporation efficiency than the conventional electroporation.

The high-density distributed three-dimensional electrode device may carry out electroporation for many cell lines in suspension or in adherence. 12 kinds of cells, 7 HEK-293A, Hela, MCF-7, A-375, Neuro-2A, U251, C2C12, 3T3-L1, CHO, MDCK, HL-60, HUVEC, are chosen to undergo electroporation, and GFP molecules are used as marker. The GFP molecules may enter into the cells and synthesize fluorescent substances in the cells if the cells are electroporated, and the synthesized fluorescent substances may glow green fluorescence under a fluorescent field such that the electroporation rate of the cells may be obtained from the number of cells in the fluorescent field divided by the total number of cells, that is to say, the higher the fluorescence intensity of the same density of cells is, the higher the efficiency of the electroporation is.

The high-density distributed three-dimensional electrode device according to the present invention may be applied in a flow device. By placing the high-density distributed three-dimensional electrode device in the flow device, the cells evenly distributed and flowing along with the flowing fluid may accept an optimal electroporation stimulation conditions when the cells experience the control of the flowing rate and pulse stimulation during passing through the electrode array, the electroporation stimulation conditions comprising the voltage amplitude value of pulse, pulse width, pulse interval, pulse number and electrode swapping control. In a continuous flowing system, except that the time when the pulses are applied to the electrodes and the time when the cells begin to flow among the electrodes need to be harmonized, the pulses and the flowing of the cell do not need a harmonization of "duration handling" between them.

The high-density distributed three-dimensional electrode device according to the present invention both has a advantage of continuous flow electroporation, in particularly being able to carry out a high-throughput electroporation for cells in a sterile closed system, and is also able to ensure that each of the cells is subjected with optimal number of pulses and most even electric field to improve the electroporation efficiency and low down the death rate.

Embodiment 2

The high-density distributed three-dimensional electrode device according to the present embodiment is similar to that of Embodiment 1 differing in the arrangement of the electrode array. In the present embodiment, the arrangement rule of the electrode array is as follow: all the electrodes are arranged to form an equilateral quadrangle shaped structure, the distances between the adjacent two electrodes are equal, the inside of the equilateral quadrangle is divided into several smaller square units by taking the distances between the adjacent two electrodes as side length, and one electrode is placed at each vertex of the squares, i.e. all the electrodes are divided into four groups, Group I, II, III, and IV, and vertexes of each square respectively belong to Group I, II, III, and IV, and these groups take turns to be applied with the electric pulse by taking one of the groups as a positive electrode and the rest groups as a negative electrode. The arrangement of the electrode array of this embodiment may be represented by slightly modifying the circumstances of Embodiment 1 shown in FIG. 4, and therefore no more figures are shown.

Embodiment 3

The high-density distributed three-dimensional electrode device provided by the present embodiment is similar to that of Embodiment 1 differing in that the arrangement of the electrode array is as follow: all the electrodes are arranged to form an equilateral hexagon structure, the distances between the adjacent two electrodes are equal, the inside of the equilateral hexagon is divided into several smaller equilateral hexagon units by taking the distances between the adjacent two electrodes as side length, and one electrode is placed at each vertex of the hexagon units, i.e. all the electrodes are divided into six groups, Group I, II, III, IV, V, and VI, and vertexes of each hexagon unit respectively belong to Group I, II, III, IV, V, and VI, and these groups take turns to be applied with the electric pulse by taking one of the groups as a positive electrode and the rest groups as a negative electrode. The arrangement of the electrode array of the present embodiment may be represented by slightly modifying the circumstances of Embodiment 1 shown in FIG. 4, and therefore no more figures are shown.

The above are only embodiments of the present invention, and are no way to limit the scope of the present invention. Any equivalent structures or process changes, or direct or indirect application on other relative technical fields by taking advantage of the content of the present invention should be covered by the scope of the present invention.

What is claimed is:

1. An electroporation method for cells in a fluid to reduce a death rate of cells, the method comprising:
   placing a three-dimensional electrode device in a flow device in which the cells flow along with the fluid, wherein the electrode device comprises an electrode array that further comprises a plurality of needle-shaped electrodes divided into at least a first group of electrodes and a second group of electrodes; and an electrode fixing assembly on which the electrode array is fixed;
   simultaneously applying electric pulses of opposite polarities to the first group of electrodes and the second group of electrodes, wherein electrodes applied with electric pulses of positive polarity are surrounded by electrodes applied with electric pulses of negative polarity; and
   subsequently reversing the polarities and simultaneously applying electric pulses of opposite polarities to the first group and the second group.

2. The electroporation method of claim 1, wherein the diameters of the electrodes are 0.01-1.2 mm, the distance between the center points of two adjacent electrodes is 0.1-2.4 mm, and the number of the electrodes is more than 5.

3. The electroporation method of claim 2, wherein the diameters of the electrodes are 0.1-0.4 mm, the distance between the center points of two adjacent electrodes is 0.2-1.5 mm, and the number of the electrodes is more than 36.

4. The electroporation method of claim 3, wherein the diameters of the electrodes are 0.3 mm, the distance between the center points of two adjacent electrodes is 1 mm, and the number of the electrodes is 37.

5. The electroporation method of claim 1, wherein the plurality of electrodes in the electrode array is arranged according to an equilateral polygon, and the distances between every two adjacent electrodes in the electrode array are equal.

6. The electroporation method of 5, wherein a shape of the electrode array is an equilateral hexagon formed by several equilateral triangles, and the electrodes are located at the vertices of the equilateral triangles.

7. The electroporation method of claim 1, wherein the material of the electrodes comprises stainless steel.

8. The electroporation method of claim 1, wherein the electrode fixing assembly comprises an electrode connecting circuit board and an electrode positioning board, wherein the electrode connecting circuit board connects the electrodes applied with the same electric pulse together, and the electrodes reside within the electrode positioning board.

9. The electroporation method of claim 1, wherein the electrodes in the electrode array are divided into three groups including the first group, the second group and a third group, wherein the first applying step further comprises applying the positive electrical pulse to the first group, and simultaneously applying the negative electrical pulse to the second group and the third group, wherein each electrode of the first group is surrounded by electrodes of the second group and the third group;

wherein the applying step after reversing the polarities further comprises: applying the positive electrical pulse to the second group and simultaneously applying the negative electrical pulse to the first group and the third group, wherein each electrode of the second group is surrounded by electrodes of the first group and the third group; and subsequently applying a positive electrical pulse to the third group and simultaneously applying a negative electrical pulse to the first group and the second group, wherein each electrode of the third group is surrounded by electrodes of the first group and the second group; and wherein the steps are performed sequentially and cyclically to achieve a homogenous electric field by superposing the resulted electric fields.

10. The electroporation method of claim 1, wherein the electrode fixing assembly comprises an electrode positioning board and an electrode connecting circuit board, wherein the electrodes are positioned by going through the electrode positioning board to reduce inconformity of distances between the electrodes, and the electrodes are connected to the electrode connecting circuit board.

11. The electroporation method of claim 1, wherein after reversing the polarities and simultaneously applying electric pulses of opposite polarities to the first group and the second group, electrodes applied with electric pulses of negative polarities are surrounded by electrodes applied with electric pulses of positive polarities.

12. An electroporation method for cells in a fluid to reduce a death rate of cells, the method comprising:

placing a three-dimensional electrode device in a flow device in which the cells flow along with the fluid, wherein the electrode device comprises an electrode array that further comprises a plurality of needle-shaped electrodes divided into at least a first group of electrodes and a second group of electrodes, and an electrode fixing assembly on which the electrode array is fixed;

simultaneously applying electric pulses of opposite polarities to the first group of electrodes and the second group of electrodes; and subsequently reversing the polarities and simultaneously applying electric pulses of opposite polarities to the first group and the second group, wherein electrodes applied with electric pulses of positive polarity are surrounded by electrodes applied with electric pulses of negative polarity.

* * * * *